United States Patent [19]

Feret

[11] Patent Number: 5,188,124
[45] Date of Patent: * Feb. 23, 1993

[54] LOW FRICTION FILM DRESSING

[75] Inventor: Ronald M. Feret, Hamilton Square, N.J.

[73] Assignee: Johnson & Johnson Consumer Products, Inc., Skillman, N.J.

[*] Notice: The portion of the term of this patent subsequent to May 7, 2008 has been disclaimed.

[21] Appl. No.: 839,733

[22] Filed: Feb. 19, 1992

Related U.S. Application Data

[63] Continuation of Ser. No. 595,339, Oct. 10, 1990, abandoned, which is a continuation of Ser. No. 382,526, Jul. 19, 1989, Pat. No. 5,012,801.

[51] Int. Cl.⁵ .............................................. A61F 13/00
[52] U.S. Cl. .................................. 128/889; 128/892; 128/893; 602/58; 602/52
[58] Field of Search ............... 128/846, 889, 888, 890, 128/891, 892, 893; 602/43, 52, 58

[56] References Cited

U.S. PATENT DOCUMENTS

| | | | |
|---|---|---|---|
| 2,608,711 | 8/1952 | Hendricks | 602/58 |
| 4,135,023 | 1/1979 | Lloyd et al. | 128/156 |
| 4,518,643 | 5/1985 | Francis | 428/131 |
| 4,612,230 | 9/1986 | Liland et al. | 428/167 |
| 4,798,604 | 1/1989 | Carter | 604/366 |
| 4,867,150 | 9/1989 | Gilbert | 128/155 |
| 5,012,801 | 5/1991 | Feret | 602/52 |

Primary Examiner—Paul Prebilic

[57] ABSTRACT

A medical dressing comprising an embossed, thin polymeric film coated on one side with a medical grade, pressure-sensitive adhesive. The embossed film has a low coefficient of friction, preferably less than about 0.6, on the outer adhesive free surface which makes the film particularly resistant to unintentional removal by rubbing forces. The film is intended primarily for use as a blister dressing, but may also be provided with an absorbent pad for use as a wound dressing.

9 Claims, 3 Drawing Sheets

LOW FRICTION FILM DRESSING

This is a continuation of application Ser. No. 07/595,339, filed Oct. 10, 1990 now abandoned, which is a continuation of application Ser. No. 07/382,526, filed Jul. 19, 1989, now U.S. Pat. No. 5,012,801.

FIELD OF THE INVENTION

This invention relates to adhesive film dressings for medical applications and, more particularly, to an elastomeric film dressing specifically adapted for use in the prevention and treatment of skin friction blisters.

BACKGROUND OF THE INVENTION

Adhesive film dressings for medical applications are well-known in the art. Transparent film dressings comprising a polyurethane film coated on one side with a medical grade, pressure-sensitive adhesive are presently used for applications such as IV catheter tapes, dermal ulcer dressings, surgical incision dressings and as occlusive covers for burns and skin donor sites. One such polyurethane film dressing is available from Johnson & Johnson, New Brunswick, N.J., under the trade name Bioclusive ® Transparent Dressing. Such polyurethane dressings are transparent, elastomeric and moisture vapor permeable while impervious to liquids and bacteria.

Typical elastomeric film dressings for medical applications are described in U.S. Pat. Nos. 4,413,621 and 4,614,183. As disclosed in these references, the polymeric films may be prepared from polyurethanes such as Goodrich Estane ® polyurethane and from elastomeric polyesters such as DuPont Hytrel ® copolyester ether elastomer, or from blends of such polyurethanes and polyesters. The films may have a thickness of from about 0.5 to 10.0 mils and are preferably from about 1 to 3 mils thick. The films preferably have a moisture vapor transmission rate of at least 100, and most preferably from about 200 to 1200 grams water per square meter per 24 hrs. (g/M$^2$/day) as determined by ASTM test E96 at 100° F. and 90° relative humidity.

The films are coated with a medical grade pressure-sensitive adhesive acceptable for long-term skin contact such as those disclosed in U.S. Pat. Nos. 3,189,581; 3,218,357; 3,325,459 and 4,112,213. These adhesives are generally copolymers of 2-ethylhexyl acrylate and vinyl acetate in ratios of approximately 60 to 70 parts of the acrylate and 30 to 40 parts of the vinyl acetate. The polymers may also contain small amounts of N-tertiary butylacrylamide as a third monomer and a cross-linking agent. A preferred adhesive is a copolymer of approximately 70% 2-ethylhexyl acrylate and 30% vinyl acetate containing from 0.01 to 1% of a silane cross-linking agent as disclosed in U.S. Pat. No. 4,112,213. Water-based adhesives and hot melt adhesives may also be employed. The adhesive is deposited on the film by solvent spreading, transfer coating, extrusion or other known method.

Polyurethane film dressings of the prior art were evaluated for use as protective coverings over friction blisters and skin areas where friction blisters were likely to develop. Although these films provided effective protection while they remained in place, problems were experienced in retaining the film on the skin surface due to the rubbing action inherent in such applications. While one possible solution was to use a more aggressive adhesive with a higher level of adhesion, this could prove disadvantageous in certain applications and on certain individuals. A more preferable solution was to utilize the presently available medical grade, pressure-sensitive adhesives and to modify the film to improve performance.

It is accordingly an object of the present invention to provide an improved adhesive film dressing particularly adapted for use as a protective covering over friction blisters or areas of the skin susceptible to the development of friction blisters. It is a further object of this invention to provide an improved adhesive film blister dressing which utilizes conventional medical grade, pressure-sensitive adhesives. These and other objects of the present invention will be apparent from the ensuing description and claims.

SUMMARY

The thin film dressings of the present invention, intended for use specifically in the prevention and treatment of skin friction blisters, comprise an embossed, elastomeric film having a thickness of from about 0.5 to 10.0 mils and coated on one surface with a medical grade, pressure-sensitive adhesive. The film is embossed to reduce the effective surface area on the adhesive-free side and to lower the coefficient of friction on that surface to less than about 1.0. The embossing also enhances the conformability of the film on irregular surfaces and reduces the tendency of the film to curl or roll up in use. As a consequence of these effects, the embossed film is retained in place on the skin surface better than comparable elastomeric films which are not embossed.

The film dressings of the present invention are suitably constructed of elastomeric polyurethane or polyester polymers, both of which materials are known for use as thin film wound dressings. The copolyester ether elastomers available from DuPont under the trade name Hytrel ® are particularly preferred since the smooth film was discovered to have a coefficient of friction less than that of polyurethane, and an embossed 1.5 mil film was found to have a coefficient of friction of less than about 0.6.

The embossed films are coated with a medical grade, pressure-sensitive adhesive which is subsequently covered with a protective release paper. The films are packaged and sterilized following conventional procedures for thin film wound dressings. The film dressings of the present invention may be offered in a variety of sizes and shapes for applications to various areas of the body subject to frictional forces which may lead to or have caused blisters to form. Common applications are to the fingers, thumb and palm of the hand and to the heel and toes of the feet. The dressings may optionally include a centrally located absorbent pad which may be particularly desirable for use over broken blisters.

DESCRIPTION OF INVENTION

The dressings of the present invention comprise thin, embossed, elastomeric films coated with a pressure-sensitive adhesive and packaged and sterilized in a ready to use form. While embossing the film is a key element of the present invention, the embossing pattern is not critical. Suitable embossing patterns and methods for embossing thin polymeric films are known in the art as disclosed for example in U.S. Pat. Nos. 3,484,835, 4,298,647 and 4,376,147. Good results have been obtained with the embossing design described in U.S. Pat. No. 3,484,835, which provides on one side a series of raised bosses between a plurality of channel-like areas extending in both the longitudinal and transverse directions of the film. The embossed film has a pattern closely simulating plain woven taffeta fabric. As disclosed in this reference, the channels in both directions are spaced apart about 0.010 inch to define raised bosses which are nominally 0.010 inch square and have a height of about 0.003 to 0.004 inches. The opposite side of the film is the negative image of the first side and includes a plurality of depressions defined by intersecting raised ridges. U.S. Pat. No. 3,484,835 is incorporated herein by reference for its teaching pertaining to embossed films and their method of manufacture.

Figure 1:
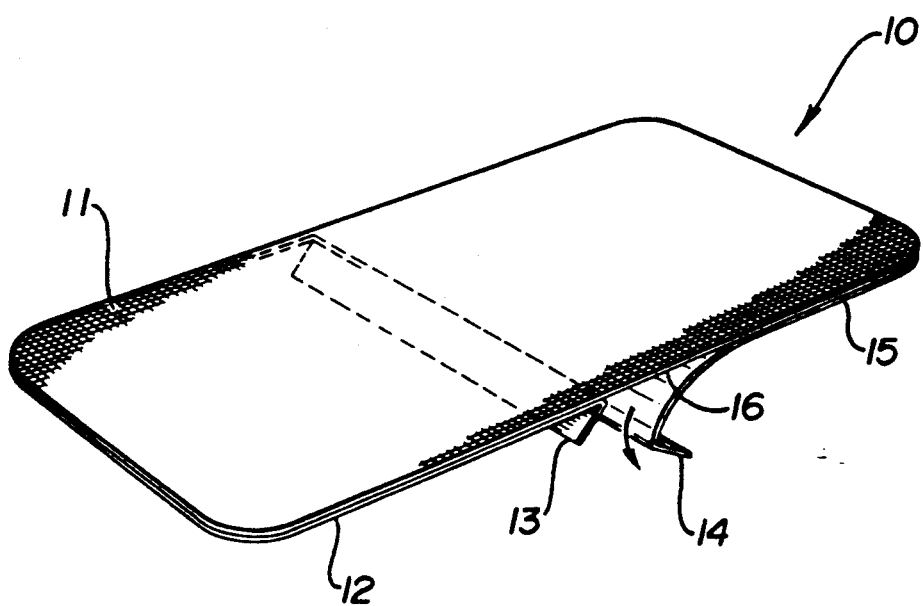
FIG. 1 is a view in perspective of a film dressing according to the present invention.

Referring now to FIG. 1, there is illustrated in perspective dressing 10 consisting of embossed film 11 coated on the underside as viewed with adhesive 16 which is a medical grade, pressure-sensitive adhesive. The adhesive surface is covered by release papers 12 and 16 which are provided with central tabs 13 and 14 to facilitate their removal. The dressing is packaged (not shown) and sterilized prior to use.

The structure of a particularly preferred embossed film is illustrated in the photomicrographs of FIG. 2 to FIG. 5 with enlargement for better understanding. The structure shown is only one of many possible variations which may be utilized with the present invention and the particular structure illustrated is presented simply to provided a better understanding of the invention. The illustrated pattern may be obtained by embossing the elastomeric film against a rubber backing roll with a steel roll engraved with a pattern of substantially square protrusions having rounded upper corners and defined by horizontally and laterally extending grooves as described in U.S. Pat. No. 3,484,835. Other embossing techniques may of course be used as, for example, the film may be passed between male and female engraved rolls rather than an engraved male roll and a rubber backing roll. The film may initially be formed as a smooth film to be followed by embossing, or may be extruded directly into an embossing station. All such methods are well known in the art.

Figure 2:
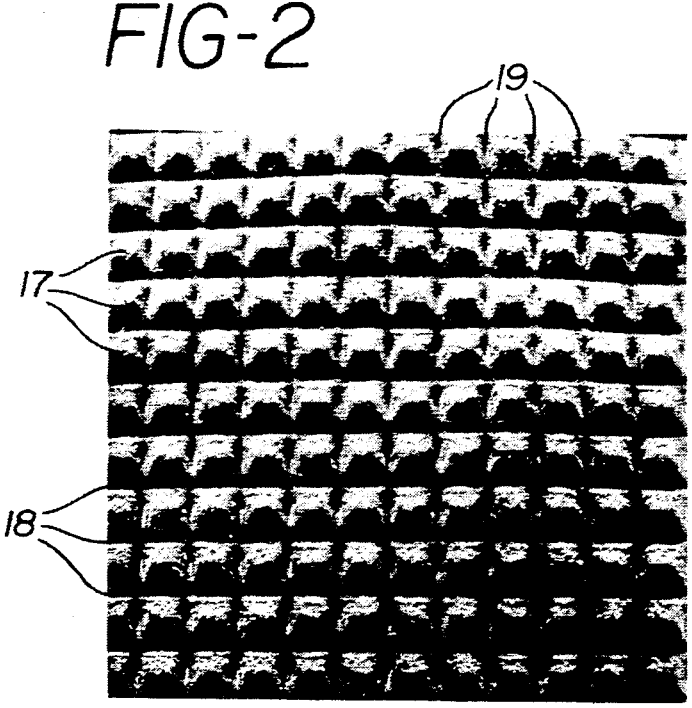
FIG. 2 is a 20× photomicrograph of an embossed film useful in the present invention showing the side to be coated with adhesive.
Figure 3:
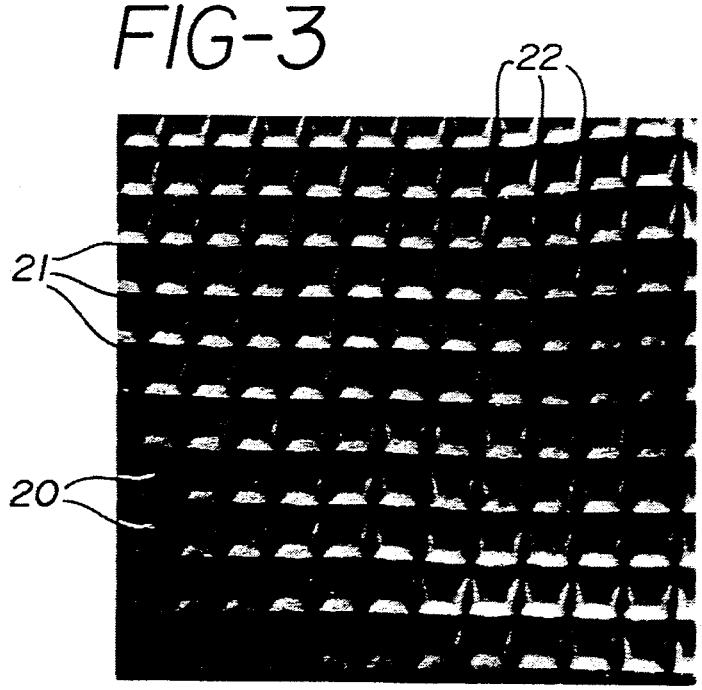
FIG. 3 is a 20× photomicrograph of the opposite side of the film of FIG. 2.
Figure 4:
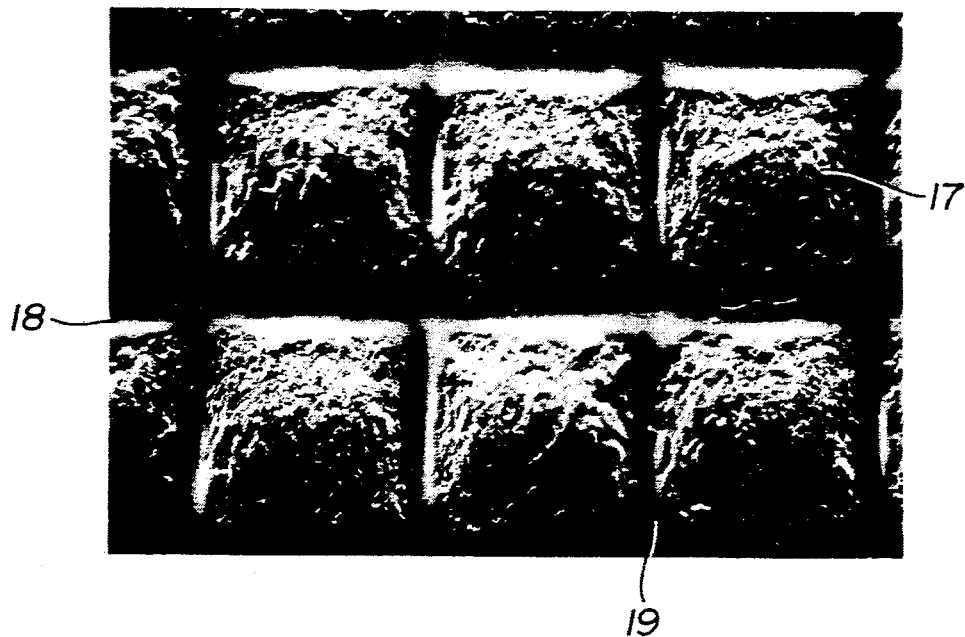
FIG. 4 is a 100× photomicrograph of the film of FIG. 2.
Figure 5:
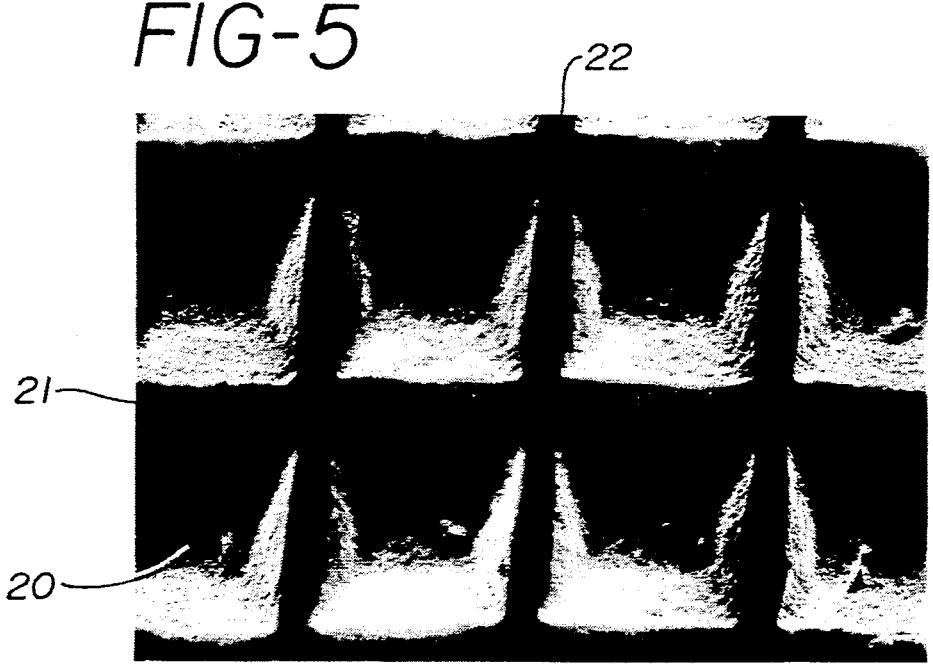
FIG. 5 is a 100× photomicrograph of the film of FIG 3.

The film illustrated in FIG. 2-FIG. 5 was prepared by extruding and embossing 1.5 mm Hytrel ® 4778 film with a steel embossing roll as described above. In the photomicrographs, FIG. 2 and FIG. 4 illustrate the positive side of the film having raised bosses 17 defined by intersecting channels 18 and 19 in a pattern corresponding to that of the steel embossing roll. The negative side of the film is illustrated in FIG. 3 and FIG. 5 where depressions 20 correspond to raised bosses 17 of FIG. 2 and FIG. 4 and ridges 21 and 22 respectively correspond to channels 18 and 19 of FIG. 2 and FIG. 4.

The positive side of the film, which is characterized by the raised bosses as illustrated in FIG. 2 and FIG. 4, forms the adhesive side of the dressings of the present invention. The embossed film is coated on the positive side with a medical grade pressure-sensitive adhesive which may be continuous over the entire surface of the film, including the area of channels 18 and 19, or may be applied as a discontinuous layer, leaving at least part of channels 18 and 19 free of adhesive. Preferably, the adhesive film is continuous over raised bosses 17 to obtain maximum skin adhesion value while leaving at least part of channels 18 and 19 adhesive-free to enhance the moisture vapor transmission properties of the dressing.

The negative side of the film as illustrated in FIG. 3 and FIG. 5 which is characterized by a plurality of depressions 20 defined by raised ridges 21 and 22 forms the outer surface of the dressing. This side of the film has a substantially reduced surface contact area as a result of the embossing which results in a corresponding reduction in the coefficient of friction on that surface. This is an important consideration for the products of the present invention since forces rubbing on the surface of the film tend to loosen the dressing and possibly cause it to roll up or simply come loose from the area it is intended to protect. Preferably, the contact area of the outer surface of the embossed film, i.e., the area of the raised surface subject to rubbing action of an adjacent surface, is less than 50% of the overall area of the film as defined by the perimeter of the film. Most preferably, the raised surface area on the outer surface of the film is less than 30% of the overall film area. In the film illustrated in FIG. 3 and 5, the raised surface area is approximately 25% of the overall film area.

Elastomeric films fabricated from the copolyester ether elastomers available from DuPont under the trademark Hytrel ® have a smooth film coefficient of friction which is less than about 0.7, while polyurethane films such as that available from Johnson & Johnson under the trade name Bioclusive ® have a smooth film coefficient of friction greater than about 1.0. Embossed films are found to have small but significantly lower coefficient of friction than the corresponding smooth films. Embossed films preferred for use in the present invention have a coefficient of friction of less than 1.0, and most preferably less than 0.6. Coefficient of friction as reported herein was determined according to the procedure of ASTM D-1894-87 using a 2-inch square foam-backed sled weighing 194 g., and covered with unbleached muslin on the sliding surface. The coefficient of friction of representative films are presented in Table I.

TABLE I

| Coefficient of Friction (COF) | | |
|---|---|---|
| Film Sample | | COF |
| 1. BIOCLUSIVE ®, | 1.3 mil, smooth | 1.09 |
| 2. HYTREL ® 4778, | 2 mil, smooth | 0.64 |
| 3. HYTREL ® 4778, | 2 mil, embossed | 0.61 |
| 4. HYTREL ® 4778, | 1.5 mil, embossed | 0.53 |

The Bioclusive ® polyurethane film (No. 1) and the 1.5 mil embossed Hytrel ® film (No. 4) of Table I were evaluated in a 24 hour wear test wherein 24 subjects wore both films on 4 body locations. Both films used the same medical grade pressure-sensitive adhesive. One inch by three inch dressings were worn on the tip of the index finger, the base of the thumb, the callous area of the palm (metacarpus) and on the back of the heel transecting the shoe line. After 24 hours, appearance was graded on a scale of 0 to 7 under a Standard Adhesion Test where 0 indicated the dressing had come completely off while 7 indicated a dressing having all four corners still securely adhered. The samples were also graded from 0 to 4 under a Modified Adhesion Test based on the tendency of the dressing to roll up where 0 indicated 100% rolled up or rolled off dressing and 4 indicated no roll up. The results of wear test and the two grading systems are presented in Table II below.

TABLE II

| | 24 Hour Wear Test | | | |
| --- | --- | --- | --- | --- |
| | STD. ADHESION TEST | | MOD. ADHESION TEST | |
| LOCATION | A | B | A | B |
| Palm | 0.0 | 0.7 | 0.0 | 0.5 |
| Index Finger | 3.0 | 3.0 | 1.2 | 2.1 |
| Thumb | 2.9 | 2.3 | 1.2 | 1.5 |
| Heel | 4.8 | 5.5 | 3.3 | 3.6 |
| Average Score | 2.68 | 2.88 | 1.42 | 1.92 |

A - Smooth Bioclusive ® Transparent Dressing
B - Embossed Hytrel ® elastomer film Dressing The data in Table II show a small but significant wear test advantage of the embossed Hytrel ® over smooth Bioclusive ® in both the Standard Adhesion Test and the Modified Adhesion Test.

The Hytrel ® copolyester ether elastomers which are the preferred materials for constructing thin film, low friction blister dressings in accordance with the present invention are described in U.S. Pat. Nos. 3,023,192, 3,651,014, 3,763,109, 3,766,146, and other patents assigned to E. I. DuPont de Nemours and Co., Wilmington, Del. The specific Hytrel ® polymer used in the above examples, identified as Hytrel ® 4778, is one of several Hytrel ® polymers offered by DuPont. Hytrel ® 4778 is a particularly preferred material because of its relatively high moisture vapor transmission rate, reported by DuPont as 1,500 g×day/M²×mil, or 1000 g per day per square meter for the 1.5 mil film evaluated above.

The present invention is directed to thin film dressings which are especially resistant to being unintentionally removed by frictional forces normally encountered in work or athletic activities. The films are specifically characterized as being elastomeric, embossed and having a low coefficient of friction on the exposed surface which is subjected to rubbing action. When the dressings include the optional absorbent pad, the elastomeric film may extend beyond the edges of the pad in all directions to form an island bandage, or in just two opposing directions to form a strip bandage. The absorbent pad may be plain or medicated, and is preferably provided with a wound release surface to prevent sticking to the wound.

The particular embodiments described above are for purposes of illustration only and are not intended to limit the present invention. Various modifications of the dressings described herein, including variations in materials, embossing patterns and dressing configurations will be apparent to those skilled in the art and all such modifications are included within the spirit and scope of the present invention.

I claim:

1. A thin film, self-adhesive dressing for the prevention and treatment of skin friction blisters comprising an embossed elastomeric film coated on one surface with a pressure-sensitive adhesive, said film having a thickness of from about 0.5 to 10 mils, a moisture vapor transmission rate of more then about 100 g/M²/day, and a coefficient of friction on the adhesive free surface of less than about 1.0.

2. The dressing of claim 1 wherein said film is embossed to provide at least one surface with a contact area of less than about 50% of the overall area of said film.

3. The dressing of claim 2 wherein the surface opposite said at least one surface is coated with a pressure-sensitive adhesive.

4. The dressing of claim 1 wherein said elastomeric film comprises a copolyester ether elastomer.

5. The dressing of claim 1 wherein said coefficient of friction of the adhesive free surface is less than 1.0.

6. The dressing of claim 1 wherein said elastomeric film comprises a copolyester ether elastomer and said coefficient of friction of the adhesive free surface is less than 0.6.

7. The dressing of claim 1 additionally including a centrally located absorbent pad on the adhesive coated surface of said elastomeric film.

8. The dressing of claim 7 wherein said elastomeric film extends beyond said absorbent pad in two opposing directions to form a strip bandage.

9. The dressing of claim 7 wherein said elastomeric film extends beyond said absorbent pad in all directions to form as island bandage.

* * * * *